(12) United States Patent
Hisatsu

(10) Patent No.: US 9,339,258 B2
(45) Date of Patent: May 17, 2016

(54) ULTRASONIC DIAGNOSIS APPARATUS

(75) Inventor: Masanori Hisatsu, Tokyo (JP)

(73) Assignee: HITACHI ALOKA MEDICAL, LTD., Tokyo (JP)

( * ) Notice: Subject to any disclaimer, the term of this patent is extended or adjusted under 35 U.S.C. 154(b) by 791 days.

(21) Appl. No.: 13/251,487

(22) Filed: Oct. 3, 2011

(65) Prior Publication Data

US 2012/0190985 A1 Jul. 26, 2012

(30) Foreign Application Priority Data

Jan. 25, 2011 (JP) ................. 2011-012701

(51) Int. Cl.
- *A61B 8/08* (2006.01)
- *G01S 7/52* (2006.01)
- *G10K 11/34* (2006.01)
- *G01S 15/89* (2006.01)

(52) U.S. Cl.
CPC ............ *A61B 8/5269* (2013.01); *G01S 7/52033* (2013.01); *G01S 7/52047* (2013.01); *G01S 7/52049* (2013.01); *G01S 7/52077* (2013.01); *G01S 15/8915* (2013.01); *G10K 11/346* (2013.01)

(58) Field of Classification Search
CPC ............ G01S 7/52049; G01S 7/52047; G01S 7/52033; A61B 8/5269
See application file for complete search history.

(56) References Cited

U.S. PATENT DOCUMENTS

| | | | |
|---|---|---|---|
| 4,815,047 A * | 3/1989 | Hart | ............................... 367/103 |
| 5,369,624 A | 11/1994 | Fukukita et al. | |
| 6,436,044 B1 | 8/2002 | Wang | |
| 7,508,737 B1 | 3/2009 | Alexandru | |
| 2005/0219096 A1 | 10/2005 | Freeman et al. | |

(Continued)

FOREIGN PATENT DOCUMENTS

| EP | 1686393 A2 | 8/2006 |
|---|---|---|
| JP | 62-90542 A | 4/1987 |

(Continued)

OTHER PUBLICATIONS

European Search Report dated Feb. 23, 2012, issued in corresponding European Patent Application No. 11007977.9 (6 pages).

(Continued)

*Primary Examiner* — Unsu Jung
*Assistant Examiner* — Saurel J Selkin
(74) *Attorney, Agent, or Firm* — Westerman, Hattori, Daniels & Adrian, LLP (57) ABSTRACT

There is provided an ultrasonic diagnosis apparatus capable of reducing an unnecessary signal component in a reception signal. A plurality of sign bits arranged in the channel direction are extracted from a plurality of element reception signals. A binarization circuit applies binarization processing to the plurality of sign bits to thereby generate a sign data array. An evaluation value computing unit computes an evaluation value (GSCF) based on a DC vicinity component contained in the sign data array on the frequency axis. This evaluation value is used to adjust the gain of the reception signal in a multiplier. With application of the binarization processing, excessive reduction of the reception signal can be prevented. Further, as the DC vicinity component is referenced, the side-lobe component can be appropriately reduced even if a certain degree of fluctuation exists in the main-lobe component.

8 Claims, 7 Drawing Sheets

(56) References Cited

U.S. PATENT DOCUMENTS

2005/0228279 A1* 10/2005 Ustuner et al. ............... 600/443
2006/0173313 A1  8/2006 Liu et al.

FOREIGN PATENT DOCUMENTS

| | | |
|---|---|---|
| JP | 62-161072 A | 7/1987 |
| JP | 2006-204923 A | 8/2006 |
| WO | 2010/018282 A1 | 2/2010 |

OTHER PUBLICATIONS

Camacho, Jorge et al., "Phase Coherence Imaging", IEEE Transactions on Ultrasonics, Ferroelectrics, and Frequency Control, May 2009, p. 958-974, vol. 56, which is cited in the specification.

Li, Pai-Chi et al., "Adaptive Imaging Using the Generalize Coherence Factor", IEEE Transactions on Ultrasonics, Ferroelectrics, and Frequency Control, Feb. 2003, p. 128-141, vol. 50, which is cited in the specification.

Japanese Office Action dated Jul. 29, 2014, issued in corresponding Japanese Patent Application No. 2011-012701 (2 pages).

Song, Tai K. et al., "Ultrasonic Dynamic Focusing Using an Analog FIFO and Asynchronous Sampling", IEEE Transactions on Ultrasonics, Ferroelectrics, and Frequency Control, May 1994, pp. 326-332, vol. 41, No. 3.

Lie, Ioan et al., "A Compact FPGA Beamformer Architecture", 2005 WSEAS International Conference on Dynamical Systems and Control, Nov. 2-4, 2005, pp. 463-466, Venice Italy.

\* cited by examiner

ULTRASONIC DIAGNOSIS APPARATUS

BACKGROUND

1. Technical Field

The present invention relates to an ultrasonic diagnosis apparatus, and more particularly to a technique of reducing an unnecessary or undesired signal component in a reception signal.

2. Background Art

Ultrasonic diagnosis apparatuses are apparatuses which form an ultrasonic diagnosis image by transmitting and receiving ultrasound to and from a living organism. In order to increase the image quality of the ultrasonic diagnosis image, it is desirable to reduce an unnecessary signal component contained in a reception signal; i.e., a side-lobe component, a grating lobe component, a noise component, or the like.

Two methods have been proposed for reducing or suppressing an unnecessary signal component contained in a reception signal after phase alignment and summing processing: one is a first method (a GCF method) for suppressing a reception signal by using a factor called a GCF (Generalized Coherence Factor) (see Pai-Chi Li, et al, "Adaptive Imaging Using the Generalized Coherence Factor", IEEE Transactions Ultrasonics, Vol. 50, No. 2, 2003), and the other is a second method (an SCF method) for suppressing a reception signal by using a factor called an SCF (Sign Coherence Factor) (see J. Camacho, et al, "Phase Coherence Imaging", IEEE trans. UFFC, vol. 56, No. 5, 2009 (WO2010/018282)).

However, both methods described above have advantages and disadvantages. From a viewpoint of enhancement of the image quality of an ultrasonic diagnosis image, it has been desired to prevent excessive suppression of a main-lobe component while effectively suppressing an unnecessary signal component such as a side-lobe component.

SUMMARY

An advantage of the present invention is to prevent excessive suppression with respect to a reception signal while reducing an unnecessary signal component contained in the reception signal.

In accordance with an aspect of the invention, there is provided an ultrasonic diagnosis apparatus including an array transducer which is composed of a plurality of transducer elements, a delay processing unit which performs delay processing with respect to a plurality of element reception signals output from the plurality of transducer elements, a summing processing unit which performs summing processing with respect to the plurality of element reception signals having been subjected to the delay processing and outputs a reception signal, a circuit which extracts a sign data array formed of a plurality of sign data items arranged in an element arranging direction, from the plurality of element reception signals having been subjected to the delay processing but not having been subjected to the summing processing, an evaluation value computing unit which computes an evaluation value based on a direct current vicinity component contained in the sign data array, and a gain adjustment unit which adjusts gain of the reception signal by using the evaluation value.

With the above structure, because a plurality of sign data items extracted from a plurality of element reception signals are used as a basis for computing an evaluation value; i.e., because a plurality of amplitude values of the plurality of element reception signals are not directly used as a basis for computing the evaluation value, there can be realized an evaluation value computation which is less vulnerable to the effects of the side-lobe component or the like, or which is less dependent on the side-lobe component. Accordingly, because excessive suppression of the reception signal caused by the side-lobe component or the like can be prevented, the possibility of generation of dark portions resulting from a strong reflector at different positions on an ultrasonic diagnosis image can be prevented or reduced. Further, with the above structure, because not only the direct current (DC) component contained in the sign data array but also the alternating current component in the vicinity of the direct current region can be used as a basis for computation of the evaluation value, even if there is a fluctuation of the main-lobe component, an evaluation value computation which is less vulnerable to such a fluctuation can be achieved. As a result, because excessive suppression of the reception signal resulting from the fluctuation of the main-lobe component can be prevented, occurrence of an "uneven phenomenon" in which a large number of fine dark portions are generated in a homogeneous medium (a tissue having uniformity) on an ultrasonic diagnosis image can be prevented or reduced. As described above, according to the above structure, it is also possible to make use of the advantages of the conventional GCF and SCF, while at the same time mitigating the disadvantages thereof. Accordingly, signal processing with a high practical value can be provided. The direct current vicinity component described above corresponds to a portion of the power spectrum on the lower side, and refers to a power component existing within a section on the frequency axis from the frequency zero (DC) to a predetermined frequency. Here, the predetermined frequency is generally set as a low frequency in the vicinity of the direct current region on the frequency axis, and it is desirable to variably set the predetermined frequency automatically or by a user.

Preferably, the ultrasonic diagnosis apparatus further includes a control unit which sets a receiving aperture which changes dynamically, with respect to the array transducer, and the evaluation value computing unit computes the evaluation value by standardizing the direct current vicinity component by using the number of transducer elements forming the receiving aperture. With the size variation of the receiving aperture, the number of reception signals which are generated; i.e., the operating transducer elements, changes, in association with which the power of the direct current vicinity component changes. Accordingly, in order to prevent inadvertent change of the gain by means of a change of the receiving aperture size, standardization of the number of operating transducer elements is desired.

Preferably, the ultrasonic diagnosis apparatus further includes a function generating unit which generates a weighting function formed of a plurality of weight values, and a weighting processing unit which performs weighting processing with respect to the plurality of element reception signals, by using the weighting function, and the evaluation value computing unit computes the evaluation value in accordance with the weighting function. Because the degree of contribution or the degree of influence of the individual element reception signals in the phase alignment and summing processing changes due to the weighting processing with respect to the plurality of element reception signals, it is desirable to take into consideration the weighting function; i.e., a plurality of weight values, at the time of computing the evaluation value. Preferably, the weighting processing unit is provided between the delay processing unit and the summing processing unit, and the circuit which extracts the sign data array extracts the sign data array from the plurality of element reception signals having been subjected to the delay processing but having not been subjected to the weighting processing. With this structure, the evaluation value can be computed appropriately, even when a negative value is included in the plurality of weight values.

Preferably, the circuit which extracts the sign data array extracts the sign data array by extracting a plurality of sign bits from the plurality of element reception signals. Alternatively, the circuit which extracts the sign data array includes a circuit which extracts an amplitude profile formed of a plurality of instantaneous amplitude values from the plurality of element reception signals, and a circuit which performs binarization processing with respect to the amplitude profile, with a hysteresis property. With the binarization processing having a hysteresis property, natural processing which does not depend on unstable amplitude behavior in the vicinity of the baseline can be performed. As is known, the binarization processing having a hysteresis property refers to processing in which separate threshold values are used for the rise and fall of the waveform. Further, it is also possible to apply ternarization processing in which signals in the vicinity of the baseline are converted to zero.

Preferably, the ultrasonic diagnosis apparatus further includes a detection unit which performs detection processing with respect to the reception signal, and the gain adjustment unit includes a multiplier which multiples the reception signal having been subjected to the detection processing by the evaluation value.

In the above structure, it is desirable to employ a configuration such that the range on the frequency axis which is referenced as the direct current vicinity components can be variably set by a user observing the ultrasonic diagnosis image or can be variably set automatically from the evaluation result of the ultrasonic diagnosis image. With the widening of the reference range, the effects with respect to the fluctuation of the main-lobe component become smaller, so that excessive suppression of the reception signal can be further prevented. With the narrowing of the reference range, effects close to those of the SCF method can be obtained.

BRIEF DESCRIPTION OF THE DRAWINGS

A preferred embodiment of the present invention will be described in detail based on the following figures, wherein.

DETAILED DESCRIPTION

A preferred embodiment of the present invention will be described in detail with reference to the accompanying drawings.

(1) Explanation of GCF Method and SCF Method

Figure 1:
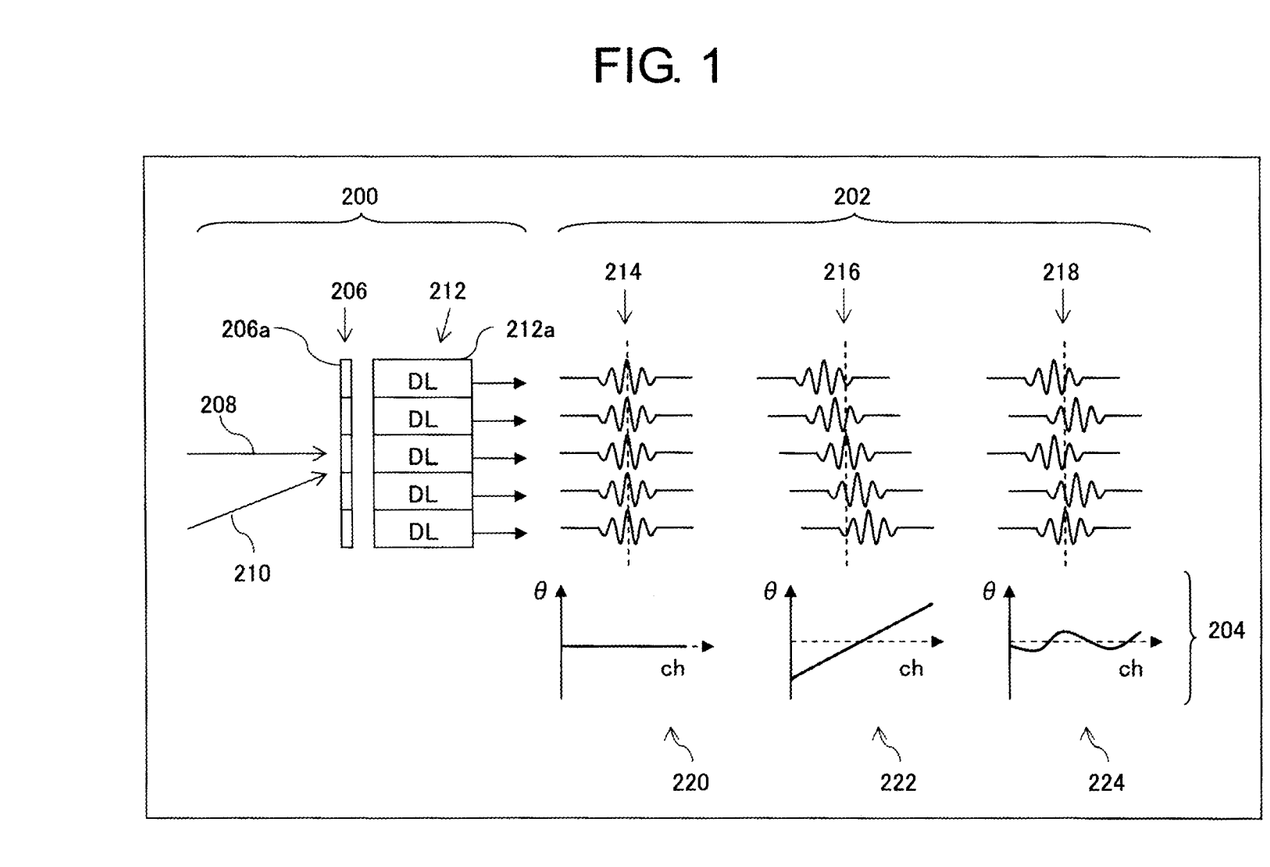
FIG. 1 is an explanatory view illustrating wave receiving processing and a reception signal array.

FIG. 1 illustrates the function of a receiving beam former in an ultrasonic diagnosis apparatus. The receiving beam former constitutes a receiving unit, or a phase alignment and summing processing unit. Reference numeral 200 represents processing of receiving waves. An array transducer 206 is composed of a plurality of transducer elements 206a arranged indicates a reflection wave (a main-lobe component) from a receiving focus point, and reference numeral 210 indicates an unnecessary wave component (which is, in this example, a side-lobe component from a strong reflector). The receiving beam former includes a delay line array 212 for delay processing. The delay line array 212 is composed of a plurality of delay lines 212a. The delay times of the individual delay lines 212a are dynamically set in a variable manner such that the ultrasound is sufficiently focused at the receiving focus point, which changes dynamically. Each delay line 212a may be formed of a FIFO memory.

In FIG. 1, reference numeral 202 indicates three element reception signal arrays corresponding to three respective cases. Each element reception signal array is formed of a plurality of element reception signals having been subjected to delay processing, which are arranged in the channel (ch) direction. Reference numeral 204 indicates three phase graphs corresponding to the three respective cases. Each phase graph is formed of a phase (corresponding to an instantaneous amplitude) of a plurality of element reception signals arranged in the channel direction. In the first case, in which main-lobe components are received, the phases of the individual element reception signals are identical (see reference numeral 220) in the element reception signal array 214 having been subjected to the delay processing. In the second case, in which side-lobe components are received, the phases of the individual element reception signals are sequentially shifted along the channel direction (see reference numeral 222) in the element reception signal array 216 having been subjected to the delay processing. The phase difference or the frequency observed in this case depends on the difference in the angle between the main-lobe direction and the side-lobe direction. In the third case, in which a variation in sonic velocity (phase aberration) is generated within an inhomogeneous medium, the phases of the individual element reception signals are turbulent (see reference numeral 224) in the element reception signal array 218 having been subjected to the delay processing. In the receiving beam former, the phase alignment and summing processing is applied to the element reception signal array having been subjected to the delay processing, to thereby suppress the unnecessary signal component. However, it is difficult to remove all the unnecessary signal components with only the phase alignment and summing processing, and therefore the reception signal (beam data) having been subjected to the phase alignment and summing processing actually contains various unnecessary signal components, which are causes of the reduction in the image quality of an ultrasonic diagnosis image.

Two methods have been proposed for reducing or suppressing an unnecessary signal component contained in a reception signal after the phase alignment and summing processing: one is a first method (a GCF method) for suppressing a reception signal by using a factor called a GCF (Generalized Coherence Factor), and the other is a second method (an SCF method) for suppressing a reception signal by using a factor called an SCF (Sign Coherence Factor).

Figure 2:
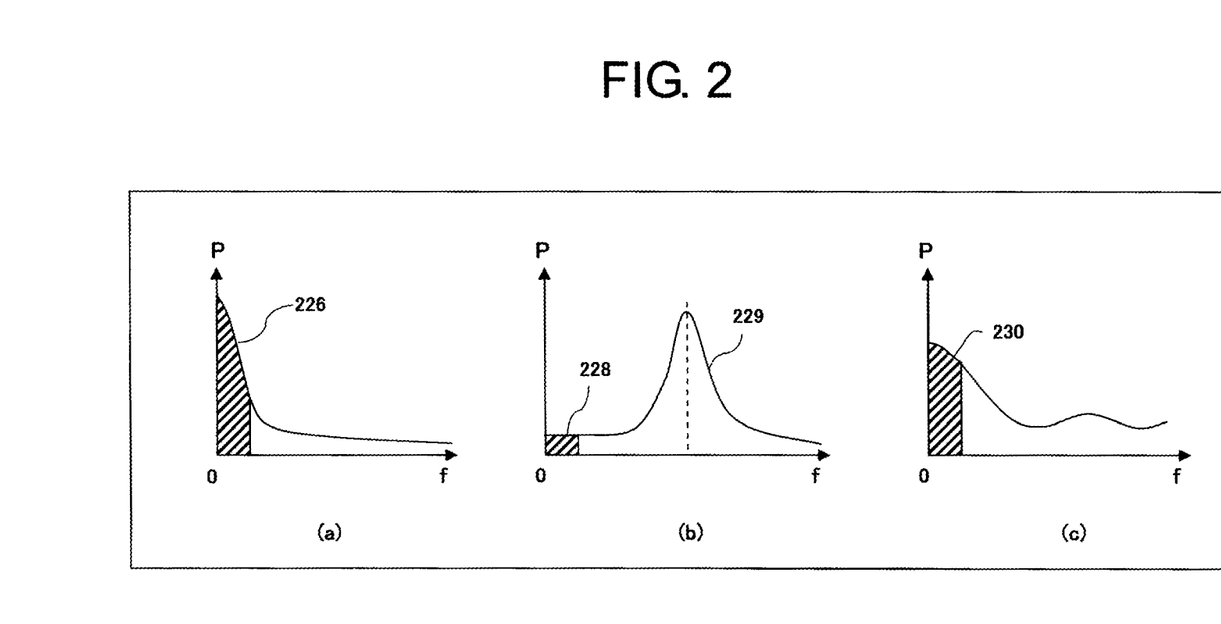
FIG. 2 is a view illustrating power spectra obtained by frequency analysis of an amplitude profile.

First, the first method will be described. A plurality of element reception signals arranged in the channel direction have a plurality of instantaneous amplitude values arranged in the channel direction at a certain time point, and these plurality of instantaneous amplitude values form an amplitude profile (corresponding to the phase graph described above). The amplitude profile is specified at individual time points (individual sampling timings), and changes dynamically with the lapse of time. By applying Fourier transformation (frequency analysis) to the amplitude profile, a power spectrum is obtained. FIG. 2 illustrates three power spectra corresponding to the above-described three cases. Specifically, FIG. 2(a) illustrates a power spectrum corresponding to the first case described above, in which the main-lobe components are dominant. FIG. 2(b) illustrates a power spectrum corresponding to the second case described above, in which the side-lobe components are dominant. FIG. 2(c) illustrates a power spectrum corresponding to the third case described above, in which turbulence of the phase caused by the phase aberration can be recognized. In the first case, because the phases are identical with each other in the element reception signal array, the main-lobe components generate a sharp peak at the DC (frequency zero) point on the frequency axis, as illustrated in FIG. 2(a). Reference numeral 226 (hatched portion) represents DC vicinity components (power components in the vicinity of DC) existing in a section from DC to a certain value. In the second case, on the other hand, a peak 229 appears at a frequency which is defined in accordance with the incoming direction (incoming angle) of the side-lobe component, as illustrated in FIG. 2(b). Numeral reference 228 represents DC vicinity components in this case. In the third case in which the phase aberration is generated, the power spectrum spreads along the frequency axis and the noise level is increased as a whole, as illustrated in FIG. 2(c). Reference numeral 230 represents the DC vicinity components in this case. With the use of the change of the power spectrum shape described above, a GCF is defined as an evaluation value, which is a factor that indicates an evaluation of the result of the phase alignment and summing processing, based on the following equation (1).

GCF=(partial power as DC vicinity components)/
(power of whole power spectrum)   (1)

In FIGS. 2(a), 2(b), and 2(c), the hatched portions 226, 228, and 230 represent values of the numerator in the above equation (1). If the amount of the main-lobe components (i.e. DC vicinity components) is large with respect to the whole power spectrum, the GCF approaches 1; otherwise, the GCF approaches 0. Accordingly, the GCF is an evaluation value indicating the ratio of presence of proper components. By using the GCF to adjust the gain of the signal after the phase alignment and summing processing, retention of the amplitude information concerning the main-lobe component and reduction in the unnecessary signal component can be achieved simultaneously.

According to the first method, as the factor is defined based on the components having a certain degree of width on the frequency axis; that is, an area within the DC vicinity section, the value of GCF is not lowered even if the signal component corresponding to the main-lobe fluctuates to some degree. Accordingly, with this first method, it is unlikely that the "uneven phenomenon" in which a large number of small dark portions are generated in a homogeneous medium occurs on the image. On the other hand, according to the first method, during the summing processing after the delay processing (corresponding to the low-pass filter processing), while the side-lobe components are suppressed, the reception signal is excessively suppressed in some cases, because the factor is determined only from the element reception signal array having not been subjected to the summing processing. Consequently, it is likely that local dark portions (low-brightness portions) are generated at the points located with the same depth as the strong reflector and also distant from the strong detector.

Next, the second method will be described. In this method, binarization processing is applied to a reception signal "si" specified by the channel number "i." Actually, by extracting a sign bit from each element reception signal, the signal represented by the following equation (2) can be obtained.

$$bi = -1 \text{ if } si < 0$$
$$+1 \text{ if } si \geq 0 \quad (2)$$

Specifically, by extracting a sign from a plurality of element reception signals in order along the channel direction (transverse direction), the above-described signal "bi" can be obtained. With the use of this signal "bi," SCF serving as an evaluation indicator indicating the degree of alignment of the phase is defined as represented by the following equation (3):

$$SCF = \left| 1 - \sqrt{1 - \left\{ \frac{1}{N} \sum_{i=0}^{N-1} b_i \right\}^2} \right|^p \quad (3)$$

In the above equation, N represents the number of receiving channels (the number of operating transducer elements forming a receiving aperture), and p is a parameter for adjusting the SCF. If the phases are identical for all the channels, SCF is 1, and the more turbulent the phases, the closer to 0 the SCF approaches. Accordingly, by using SCF to adjust the gain of the reception signals after the phase alignment and summing processing, unnecessary signal components can be reduced.

Figure 3:
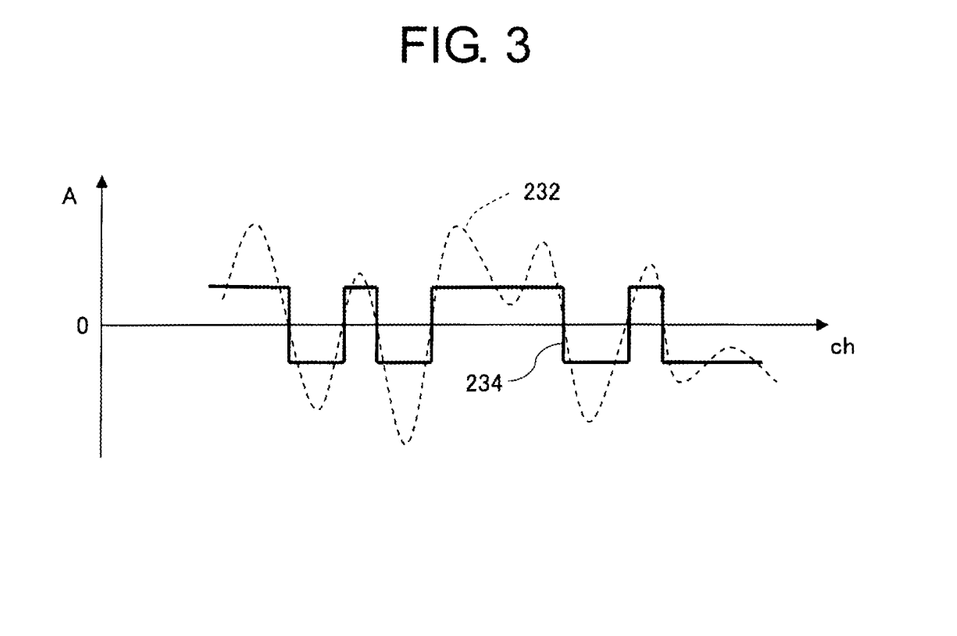
FIG. 3 is a view illustrating binarization processing.
Figure 4:
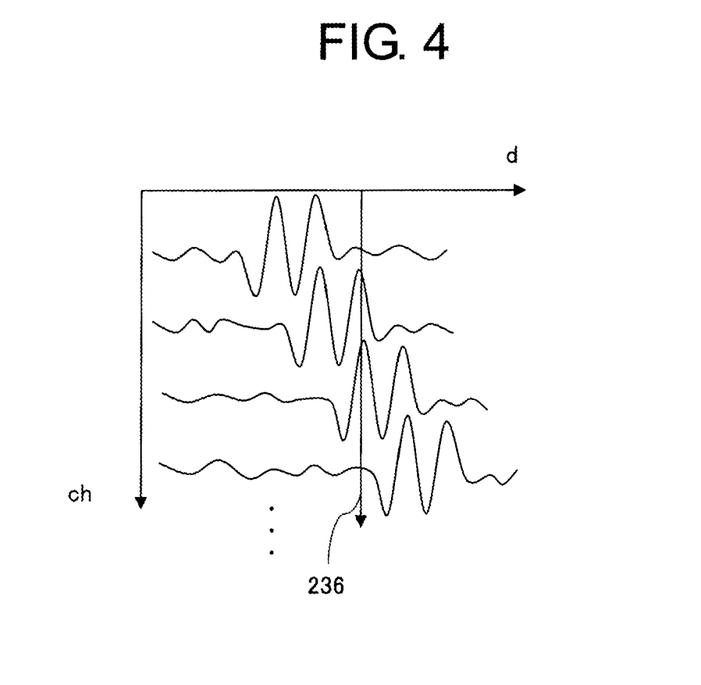
FIG. 4 is a view illustrating an element reception signal array containing a grating-lobe component.

FIG. 3 illustrates the amplitude profile 232 in a broken line. The amplitude profile 232 is formed of a plurality of amplitude values at specific timings, which are extracted from the element reception signal array after the delay processing. In FIG. 3, the horizontal axis indicates the channel and the vertical axis indicates the amplitude. By applying binarization processing to the amplitude profile, a sign data array 234 indicated by solid line can be obtained. In the case of normal pulse wave transmission, an element reception signal array formed of grating lobe components as illustrated in FIG. 4 can be obtained. In FIG. 4, the horizontal axis indicates the depth and the vertical axis indicates the channel. A plurality of waveforms represent a plurality of element reception signals after the delay processing. With regard to a certain time point (corresponding to a certain depth) 236, the phases are substantially identical only in several channels (in the example of FIG. 4, the peaks match in two channels). Because the amplitude values in these several channels are greater than the amplitude values of other channels at the same time point, in the case of using GCF, signals in these several channels dominantly contribute to the factor, so that a large GCF is obtained. In the case of SCF, on the other hand, because the amplitude value in each channel is binarized as described above, the value of the factor is not dependent on the large amplitude values but rather is dependent on the amplitude values in a great number of other channels. In the example case illustrated in FIG. 4, in which SCF has a small value, the effect of reduction of the grating lobe components is increased when SCF is used, as compared to when GCF is used. In this sense, the degree of improvement of the image quality is higher when SCF is used. On the other hand, as the main-lobe component also fluctuates due to influences of the phase aberration or due to influences of speckles caused by a scatterer, when SCF is small because of such a fluctuation, the above-described "uneven phenomenon" is likely to be generated. According to the above equation (3) for obtaining SCF, in which only DC in the power spectrum is used to calculate the factor, the greater the amount of components which are out of DC, the smaller the SCF. In the case of using GCF, on the other hand, components in the region in the vicinity of DC are also taken into consideration, slight fluctuation of the main-lobe component does not affect the factor.

As described above, according to the GCF method, in which, because the evaluation value is computed based on the power of DC vicinity components having a certain degree of width on the frequency axis, the evaluation value is not lowered even when the phase of the main-lobe fluctuates to some degree, excessive suppression of the main-lobe can be prevented even with such a fluctuation. On the other hand, with the GCF method, while the side-lobe components are to-be reduced by the summing processing after the delay processing, the evaluation value is computed from a plurality of element reception signals after the delay processing without consideration of such a reduction in the side-lobe components. Consequently, when this evaluation value is used to adjust the gain of the reception signal having been subjected to the delay processing and the summing processing, the problem of excessive reduction of the reception signals would occur without fail.

According to the SCF method, on the other hand, as the size of amplitude of each element reception signal is not considered and only the number of each sign matters, not the several channels in which the phases are relatively identical, but other channels are dominantly considered in the grating lobe, so that the effect of reduction of the grating lobe, which is greater than that obtained in the GCF method, can be expected. However, there are cases in which even the main-lobe components are out of the DC vicinity region to be evaluated, due to the influence of a certain degree of phase aberration or speckles caused by a scatterer. As a result, the "uneven phenomenon" described above is likely to occur on the tomographic image. In such cases, image formation of the main-lobe components is impaired.

(2) Explanation of New Method (GSCF Method)

The ultrasonic diagnosis apparatus according to the present embodiment obtains a sign data array by applying binarization processing to an amplitude profile which is composed of a plurality of instantaneous amplitude values extracted from an element reception signal array, calculates a GSCF (Generalized Sign Coherence Factor) as an evaluation value from the power value in the vicinity of DC of the sign data array, and adjusts the gain of a reception signal having been subjected to the phase alignment and summing processing, by using the evaluation value. With the use of GSCF, the disadvantages of the GCF method and the SCF method can be compensated while obtaining the advantages of both methods. Obviously, the present invention is not limited to a method in which GSCF is used, and includes general methods for determining the evaluation value in accordance with the DC vicinity components obtained in the case where a sign data array after the binarization processing is expanded on the frequency axis.

Figure 5:
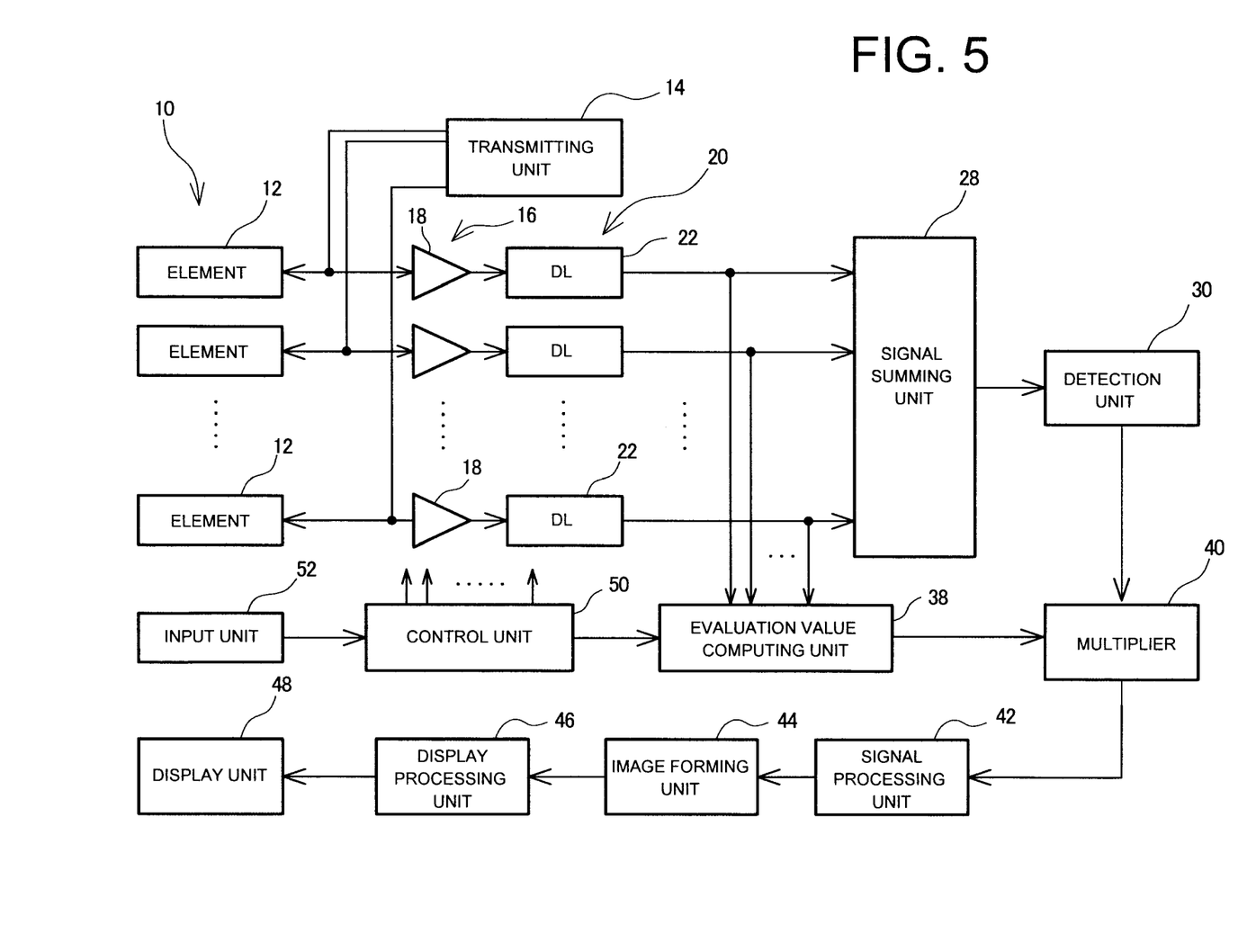
FIG. 5 is a block diagram illustrating a structure of an ultrasonic diagnosis apparatus according to an embodiment.

FIG. 5 is a block diagram illustrating a whole structure of an ultrasonic diagnosis apparatus according to the present embodiment. This ultrasonic diagnosis apparatus is used in the medical field and forms an ultrasonic diagnosis image based on a reception signal obtained by transmitting and receiving ultrasound with respect to a living organism. In the present embodiment, a B-mode tomographic image is formed as the ultrasonic diagnosis image. As a matter of course, a Doppler image or the like may be formed. This ultrasonic diagnosis apparatus has a function of suppressing undesired or unnecessary signal components described above.

Referring to FIG. 5, an array transducer 10 is disposed within an ultrasonic probe and is composed of a plurality of transducer elements 12 which are arranged in a straight line. Obviously, the transducer elements 12 may be arranged in an arc shape. Ultrasonic beams (transmitting beams and receiving beams) are formed by using the plurality of transducer elements 12 and are electronically scanned. Electronic scanning methods including an electronic sector scanning method, an electronic linear scanning method, or the like are known. A 2D array transducer can be used in place of a 1D array transducer.

A transmitting unit 14 is a transmitting beam former. Specifically, the transmitting unit 14 supplies a plurality of transmitting signals having a predetermined delay relationship to the plurality of transducer elements 12 at the time of transmission. In this manner, transmitting beams are formed. At the time of reception, reflection waves from within the living organism are received by the array transducer 10. In this manner, a plurality of reception signals (element reception signals) are generated and output to an amplification unit 16. The amplification unit 16, a delay unit 20, and a signal adding unit 28 form a receiving unit, which is a receiving beam former.

The amplification unit 16 is composed of a plurality of amplifiers 18. On the downstream side of the amplification unit 18, the delay unit 20, which is composed of a plurality of delay devices 22 which execute delay processing (phase alignment processing), is provided. A delay time, that is delay data, to be supplied to each delay device 22 is supplied from a control unit 50. An apodization processing unit or a weighting processing unit may be provided on the downstream of the delay unit 20. A plurality of reception signals (a plurality of element reception signals) after the delay processing are input to the signal summing unit 28 serving as a summing processing unit in which the plurality of reception signals after the delay processing are summed to generate a reception signal (beam data). The phase alignment and summing processing (by the signal summing unit 28) is processing for electronically forming a receiving beam. The reception signal after the phase alignment and summing processing is output to a detection unit 30, which is a known circuit which performs detection processing. An input unit 52 is connected to the control unit 50. In the present embodiment, in order to perform suppression of the unnecessary signal component, an unnecessary signal component suppression unit is provided. Specifically, the unnecessary signal component suppression unit includes an evaluation value computing unit 38 and a multiplier 40.

Figure 6:
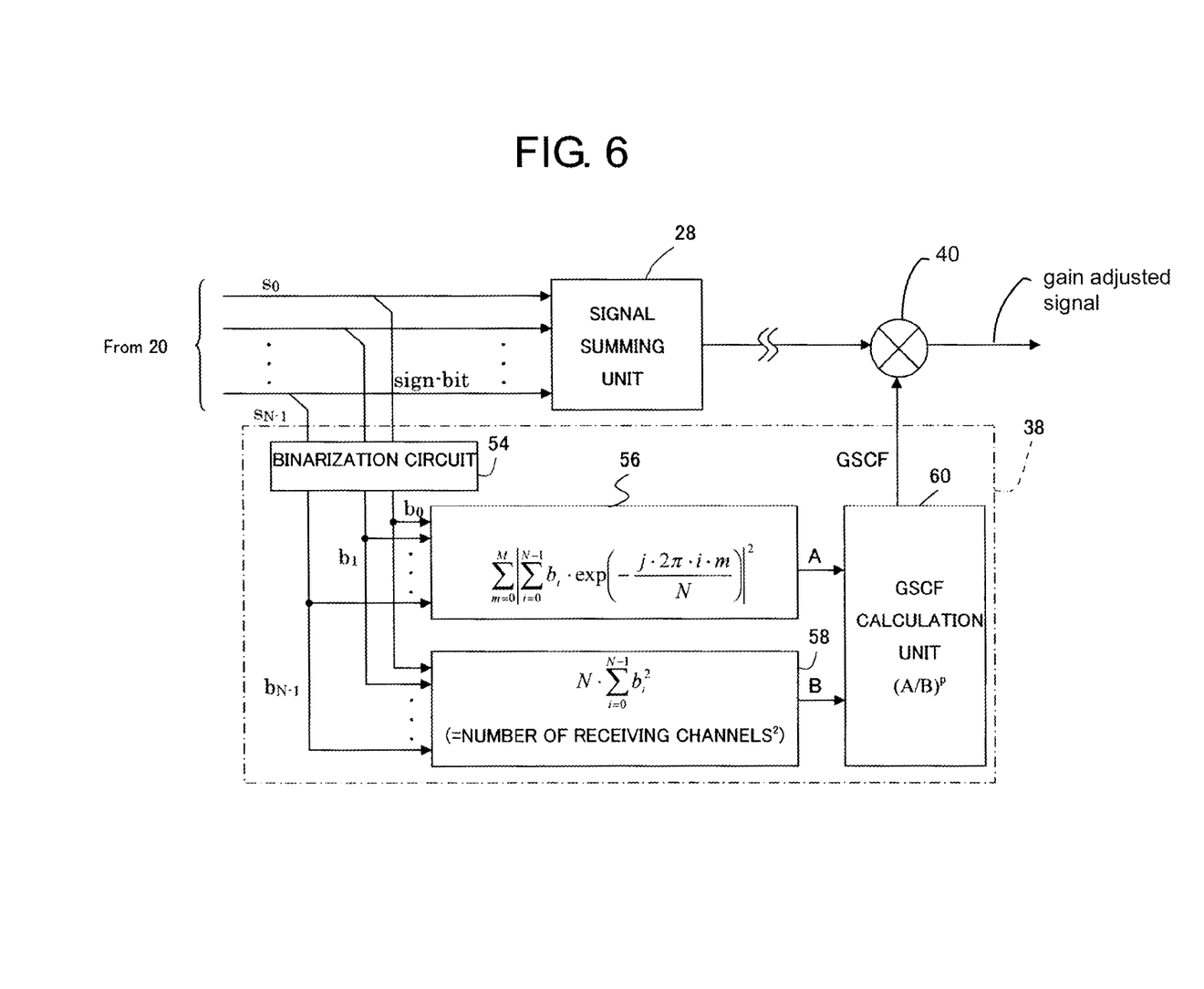
FIG. 6 is a block diagram illustrating a first example structure of an evaluation computing unit.
Figure 9:
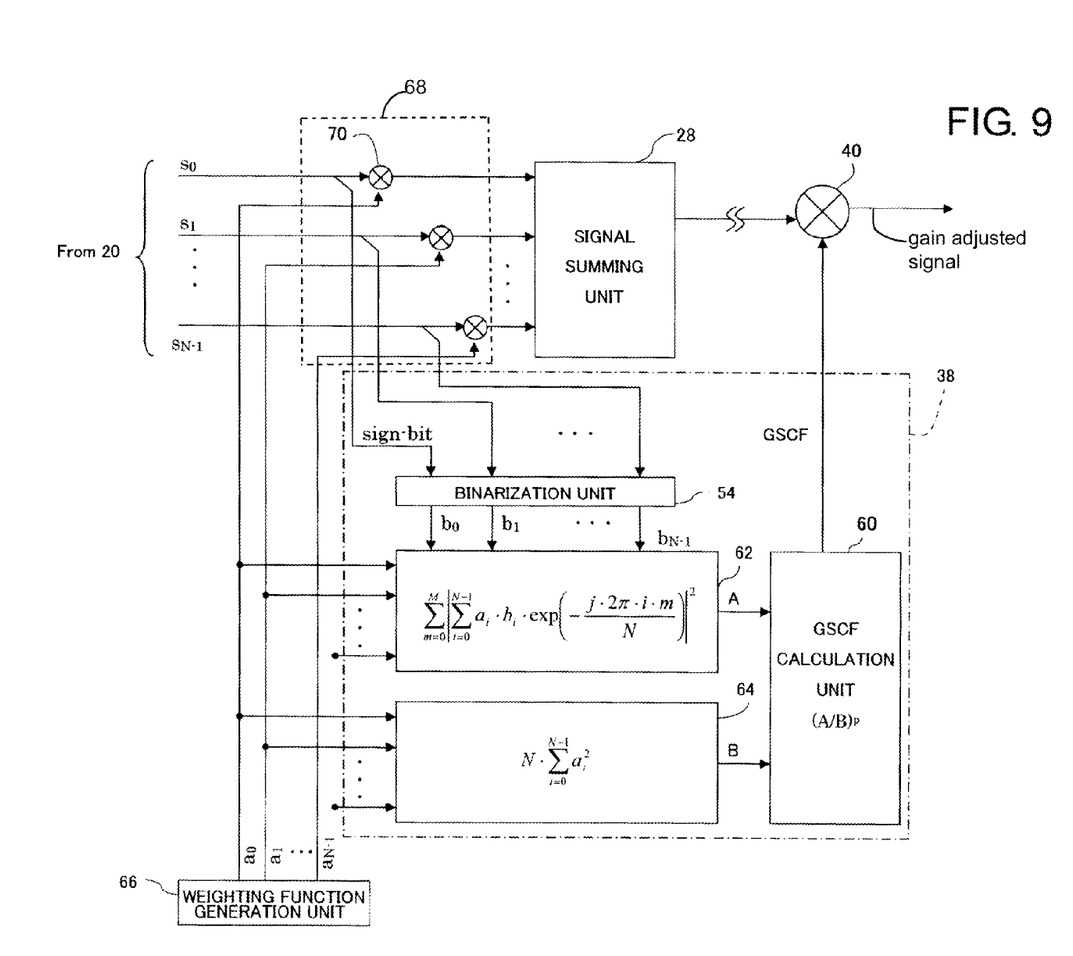
FIG. 9 is a block diagram illustrating a second example structure of the evaluation value computing unit.

The multiplier 40, serving as a gain adjustment unit, performs gain adjustment with respect to the reception signal after the detection. As shown in FIGS. 5, 6, and 9, the multiplier 40 multiplies the reception signal by GSCF. However, the gain adjustment may be performed with respect to the reception single before the detection. The gain adjustment is performed based on the new evaluation value (GSCF) which will be described below. For example, when the evaluation value is 1, the gain is 1, in which case suppression of the amplitude is not performed and the reception signal is maintained. The reception signal is suppressed when an evaluation value smaller than 1 is supplied. The evaluation value is computed in real time for individual time points, so that the gain of the reception signal is dynamically variable.

A signal processing unit 42 is a module which applies various signal processing operations such as logarithmic compression to the reception signal. An image forming unit 44 is composed by a digital scan converter (DSC), and forms a two-dimensional tomographic image (B-mode tomographic image) based on the plurality of reception signals (beam data). The DSC has a coordinate conversion function, an interpolation processing function, or the like. The image data thus generated is transmitted to a display unit 48 via a display processing unit 46. The display unit 48 displays an ultrasonic diagnosis image. The control unit 50 controls the operation of each of the components illustrated in FIG. 5. The control unit 50 has a transmission/reception control function, particularly a function of setting a receiving aperture on the array transducer. Normally, a receiving focus point is variably set dynamically on the ultrasonic beam, and the receiving aperture is variably set in steps accordingly.

The evaluation value computing unit 38 will be described. FIG. 6 illustrates a first structure example of the evaluation value computing unit. The peripheral structure will be first described. The element reception signals in the element reception signal array after the summing processing are summed in the signal summing unit 28 to form a reception signal (beam data), and the multiplier 40 applies gain adjustment processing to the reception signal.

Figure 7:
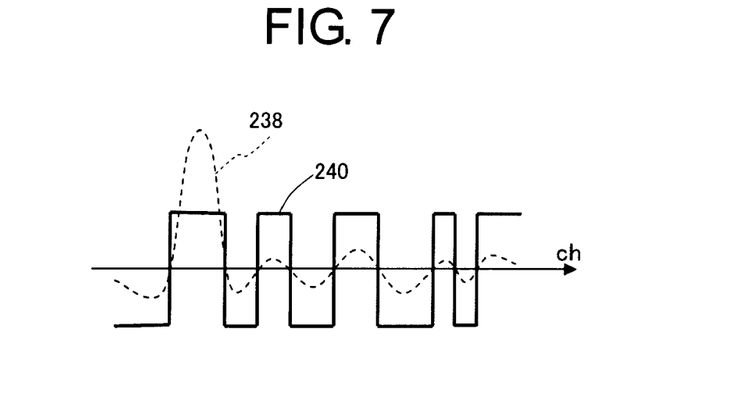
FIG. 7 is a view illustrating binarization processing with respect to an element reception signal containing a grating-lobe component.

A plurality of sign bits extracted from the plurality of element reception signals are input to the evaluation value computing unit 38. More specifically, the format of each element reception signal is converted from the analog signal format to the digital signal format by a plurality of A/D converters which are not illustrated. With this processing, the instantaneous amplitude values of the individual element reception signals are represented by a plurality of bit strings. One bit in the bit string is a sign bit indicating positive or negative. A plurality of sign bits arranged in the channel direction form a sign data array. A binarization circuit 54 applies binarization processing to each sign bit. Actually, in accordance with the above equation (2), the binarization circuit 54 converts a sign bit 1 to sign data 1, and changes a sign bit 0 to sign data −1. However, this processing can be omitted. The sign data array after the binarization processing is input to operation units 56 and 58. FIG. 7 illustrates binarization processing with respect to a reception signal containing a grating lobe component. The waveform indicated by a dotted line designated by reference numeral 238 represents an amplitude profile formed of a plurality of instantaneous amplitudes arranged in the channel direction at a certain timing. The waveform indicated by a solid line designated by numeral reference 240 represents a signal after the binarization processing is applied to the amplitude profile. While in the amplitude profile the several peaks originating from the grating lobe components match one another, because detailed amplitude values are removed by the binarization processing, the ratio of existence of the grating lobe components is small in the signal after the binarization processing.

Referring back to FIG. 6, the sign data array after the binarization processing is input to the operation units 56 and 58, which are modules that compute the numerator and the denominator in the following equation (4):

$$GSCF = \left[\frac{\text{power value of DC vicinity components of binary signal}}{\text{whole power value of binary signal}}\right]^p \quad (4)$$

$$= \left[\frac{\sum_{m=0}^{M}\left|\sum_{i=0}^{N-1} b_i \cdot \exp\left(-\frac{j \cdot 2\pi \cdot i \cdot m}{N}\right)\right|^2}{N \cdot \sum_{i=0}^{N-1} b_i^2}\right]^p$$

The operation units 56 and 58 described above may be formed of hardware or may be implemented as functions of software. In the above equation (4), the numerator represents the power value of the DC vicinity components of a binary signal; i.e., the power value existing within a section M from DC (frequency 0) to a certain frequency value, on the frequency axis after Fourier expansion. In the above equation (4), the denominator corresponds to a whole power value of a binary signal, and actually corresponds to a square of the number of receiving channels. Accordingly, while the denominator can be omitted, it is nevertheless desirable to vary the denominator in accordance with a variation of the receiving aperture. While the operation unit 56 may have an FFT (fast Fourier transform) function, it is sufficient that the operation unit 56 has a circuit structure for implementing the equation (4) because it is only necessary to obtain the power value of the DC vicinity components. With this structure, the volume of operation or the circuit scale can be reduced.

An operation unit 60 is a module which computes GSCF serving as an evaluation value; i.e., a gain adjustment factor, by using the numerator A and the denominator B in the equation (4). In this case, the parameter p in the equation (4) operates as an index. The degree of suppression can be variable by using this parameter P. It is also possible to variably set the above-described M to change the degree and content of the gain adjustment. The GSCF which is computed is output as a gain value to the multiplier 40.

Figure 8:
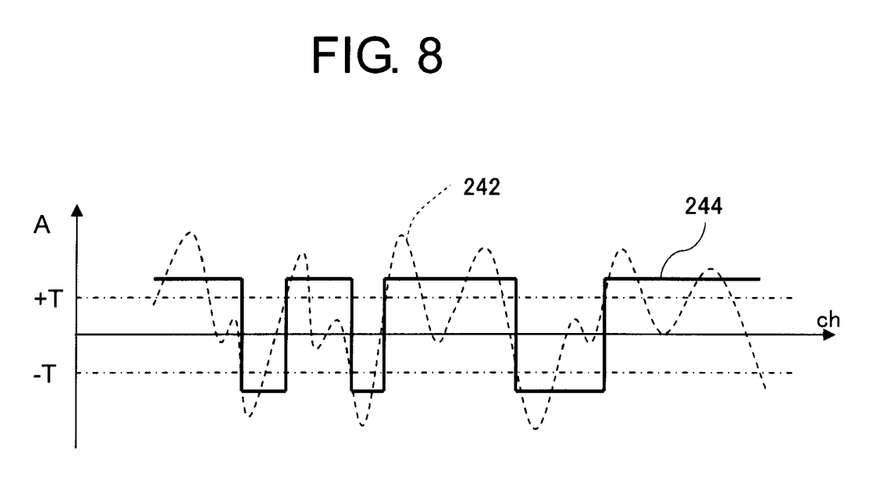
FIG. 8 is a view illustrating binarization processing having a hysteresis property.

When performing the above-described binarization processing, the binarization processing having a hysteresis property as illustrated in FIG. 8 may be used. In FIG. 8, +T is a first threshold value which functions only with respect to an amplitude change from a lower value to an upper value, and −T is a second threshold value which functions only with respect to an amplitude change from an upper value to a lower value. With this structure, a binary signal 244 can be obtained from an amplitude profile 242. Here, it is also possible to apply ternarization processing for forcedly setting a signal near the baseline to 0.

FIG. 9 illustrates a second example structure of the evaluation value computing unit 38. In FIG. 9, elements which are the same as those in the first example structure illustrated in FIG. 6 are designated by the same reference numerals and will not be described again. In this example structure, an array of weight values generated by a weighting function generator 66 is supplied to a multiplication unit (weighting processing unit) 68. The multiplication unit 68 is composed of a plurality of multipliers 70 provided corresponding to a plurality of element reception signals. Each multiplier 70 multiples each element reception signal by a weight value for apodization (weighting processing in the weighting processing unit). Variation of the aperture may be performed with this apodization. A sequence formed of a plurality of weight values is also input to an operation unit 62 and an operation unit 64. In the operation unit 62, the weight value is multiplied by the power of the DC vicinity component. In the operation unit 64, a plurality of weight values are summed. This processing is based on the following equation (5):

$$GSCF = \left[\frac{\sum_{m=0}^{M}\left|\sum_{i=0}^{N-1} a_i \cdot b_i \cdot \exp\left(-\frac{j \cdot 2\pi \cdot i \cdot m}{N}\right)\right|^2}{N \cdot \sum_{i=0}^{N-1} a_i^2}\right]^P \quad (5)$$

In the structure illustrated in FIG. 9, a plurality of sign bits are extracted before being input to the multiplication unit 68. With this structure, even if a weight value is a negative value, proper processing can be performed. However, if only a positive value is adopted for the weight value, a plurality of sign bits may be extracted from the stages downstream of the multiplication unit 68.

According to the new method described above, because the amplitude information is eliminated by the binarization processing with respect to each element reception signal, the effect of suppression of unnecessary signals, which is similar to that of the SCF method, can be obtained. Further, because the power spectrum is changed by the binarization processing of each element reception signal so that even a side-lobe component has a certain degree of power in the vicinity of DC, excessive suppression of the amplitude, which is a disadvantage of the GCF method, can be prevented. Also, with the new method described above, as the evaluation value is calculated by using the DC vicinity components, similar to the GCF method, the problem caused by fluctuation, which is a disadvantage of the SCF method, can be solved. More specifically, because the evaluation value is not lowered significantly even if the main-lobe component fluctuates, the uneven phenomenon can be prevented or improved. Here, if a square of the number of channels is used as the denominator in the above equation (4), the amount of operation can be reduced.

While the preferred embodiment of the present invention has been described using specific terms, such description is for illustrative purposes only, and it is to be understood that changes and variations may be made without departing from the spirit or scope of the appended claims.

What is claimed is:

1. An ultrasonic diagnosis apparatus comprising:
   an array transducer which is composed of a plurality of transducer elements;
   a delay processor which performs delay processing with respect to a plurality of element reception signals output from the plurality of transducer elements;
   a summing processor which performs summing processing with respect to the plurality of element reception signals having been subjected to the delay processing and outputs a reception signal, the plurality of element reception signals having been subjected to the delay processing are summed to generate the reception signal during the summing processing;
   a circuit which extracts a sign data array formed of a plurality of sign data items arranged in an element arranging direction, from the plurality of element reception signals having been subjected to the delay processing but not having been subjected to the summing processing;
   an evaluation value computing circuit which computes an evaluation value based on a direct current vicinity component contained in the sign data array in accordance with a weighting function for apodization, wherein the direct current vicinity component is a power component existing within a section from the frequency zero to a predetermined frequency in a power spectrum of the sign data array; and
   a gain adjustment unit which adjusts gain of the reception signal by multiplying the reception signal by the evaluation value.

2. The ultrasonic diagnosis apparatus according to claim 1, wherein the evaluation value computing unit computes the evaluation value by standardizing the direct current vicinity component by using the number of transducer elements forming a receiving aperture which changes dynamically with respect to the array transducer.

3. The ultrasonic diagnosis apparatus according to claim 1, further comprising: and a weighting processor which performs weighting processing with respect to the plurality of element reception signals, by multiplying each element reception signal by a weight value in accordance with the weighting function for apodization.

4. The ultrasonic diagnosis apparatus according to claim 3, wherein the weighting processor is provided between the delay processor and the summing processor, and the circuit which extracts the sign data array from the plurality of element reception signals having been subjected to the delay processing but having not been subjected to the weighting processing.

5. The ultrasonic diagnosis apparatus according to claim 1, wherein the circuit extracts the sign data array by extracting a plurality of sign bits from the plurality of element reception signals.

6. The ultrasonic diagnosis apparatus according to claim 1, wherein
   the circuit which extracts the sign data array includes:
   a circuit which extracts an amplitude profile formed of a plurality of instantaneous amplitude values from the plurality of element reception signals; and
   a circuit which performs binarization processing with respect to the amplitude profile, with a hysteresis property.

7. The ultrasonic diagnosis apparatus according to claim 1, further comprising:
   a circuit which performs detection processing with respect to the reception signal,
   wherein the gain adjustment unit includes a multiplier which multiplies the reception signal having been subjected to the detection processing by the evaluation value.

8. The ultrasonic diagnosis apparatus according to claim 1, wherein the direct current vicinity component is variably set.

* * * * *